(12) United States Patent
Martin et al.

(10) Patent No.: US 10,472,278 B2
(45) Date of Patent: Nov. 12, 2019

(54) ANTIMICROBIAL AND STRENGTHENED-GLASS ARTICLES THROUGH PRESSURIZED ION EXCHANGE

(71) Applicant: CORNING INCORPORATED, Corning, NY (US)

(72) Inventors: Arthur Winston Martin, Horseheads, NY (US); Carlton Maurice Truesdale, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 322 days.

(21) Appl. No.: 15/303,143

(22) PCT Filed: Apr. 7, 2015

(86) PCT No.: PCT/US2015/024629
§ 371 (c)(1),
(2) Date: Oct. 10, 2016

(87) PCT Pub. No.: WO2015/157221
PCT Pub. Date: Oct. 15, 2015

(65) Prior Publication Data
US 2017/0029325 A1    Feb. 2, 2017

Related U.S. Application Data (60) Provisional application No. 61/977,692, filed on Apr. 10, 2014.

(51) Int. Cl.
*C03C 21/00* (2006.01)
*C03C 10/00* (2006.01)
(Continued)

(52) U.S. Cl.
CPC .......... *C03C 21/005* (2013.01); *A01N 59/16* (2013.01); *C03C 4/18* (2013.01); *C03C 10/00* (2013.01);
(Continued)

(58) Field of Classification Search
CPC ..................... C03C 21/002; C03C 21/005
See application file for complete search history.

(56) References Cited

U.S. PATENT DOCUMENTS 3,296,260 A * 1/1967 Knoth, Jr. ............... C06B 47/10
544/69
3,529,946 A 9/1970 Hellmuth et al.
(Continued)

FOREIGN PATENT DOCUMENTS

| EP | 0007218 A1 | 1/1980 |
|---|---|---|
| KR | 201300357 | 1/2013 |
| KR | 2013127884 | 11/2013 |

OTHER PUBLICATIONS

Patent Cooperation Treaty International Notification of Transmittal of the International Search Report and the Written Opinion of the International Searching Authority, international application No. PCT/US2015/024629: dated Oct. 1, 2015, 14 pages.
(Continued)

*Primary Examiner* — Jodi C Franklin
(74) *Attorney, Agent, or Firm* — Kevin M. Johnson (57) ABSTRACT

A method of treating a substrate in a pressure vessel that includes the steps: preparing an ion-exchange bath with a bath composition that comprises a polar solvent and a plurality of ion-exchanging ions in a vessel; submersing a substrate having an outer region containing a plurality of exchangeable ions in the bath; pressurizing the bath in the vessel to a predetermined pressure substantially above ambient pressure; heating the bath in the vessel to a predetermined temperature; and treating the substrate for a prede-
(Continued)

termined ion-exchange duration at the predetermined pressure and temperature such that a portion of the plurality of exchangeable ions is exchanged with a portion of the ion-exchanging ions. The substrate can consist essentially of a glass, glass-ceramic or ceramic substrate composition, and the predetermined ion-exchange duration, temperature and pressure can each be selected based at least in part on the substrate composition and the bath composition.

17 Claims, 4 Drawing Sheets (51) Int. Cl.
C03C 4/18 (2006.01)
A01N 59/16 (2006.01)
(52) U.S. Cl.
CPC ........ *C03C 21/002* (2013.01); *C03C 2204/02* (2013.01)

(56) References Cited

U.S. PATENT DOCUMENTS

| | | | |
|---|---|---|---|
| 3,844,754 A | 10/1974 | Grubb et al. | |
| 4,156,755 A | 5/1979 | Rinehart | |
| 4,191,547 A * | 3/1980 | Wu | C03C 3/085 365/119 |
| 4,894,303 A * | 1/1990 | Wu | C03C 3/085 430/13 |
| 5,285,517 A * | 2/1994 | Wu | C03C 3/085 359/885 |
| 6,844,669 B2 | 1/2005 | Sugawara et al. | |
| 8,586,492 B2 | 11/2013 | Barefoot et al. | |
| 8,969,226 B2 | 3/2015 | Dejneka et al. | |
| 9,346,703 B2 | 5/2016 | Bookbinder et al. | |
| 2008/0156232 A1* | 7/2008 | Crudden | A01N 59/16 106/725 |
| 2008/0254373 A1* | 10/2008 | Wu | G03H 1/02 430/2 |
| 2008/0305153 A1* | 12/2008 | Wang | A01N 59/16 424/443 |
| 2014/0106172 A1 | 4/2014 | Dejneka et al. | |
| 2014/0356406 A1* | 12/2014 | Patil | A01N 25/04 424/411 |
| 2014/0356605 A1* | 12/2014 | Adib | C03C 21/001 428/220 |
| 2014/0370302 A1* | 12/2014 | Amin | C03C 21/005 428/426 |
| 2014/0370303 A1* | 12/2014 | Jin | C03C 21/005 428/426 |
| 2015/0147775 A1 | 5/2015 | Fiacco et al. | |

OTHER PUBLICATIONS

Yunqui, H., Duvigneaud, P.H., & Plumat, E, "Mechanical Strength improvement of glass by ion exchange in the solid state" Int. Symp. on glass. Proc. Second Beijing symp., Sep. 3-7, 1984.
Stefan, K., Bo, J., "The technology of chemical glass strengthening—a review", Glass Technol. A, Apr. 2010, 51(2), 41-54.
Mallick, K.K, Holland, D., "Strengthening of container glasses by ion-exchange dip coating", Journal of Non-Crystalline Solids 351 (2005) 2534-2536.
Vincenzo M. Sglavo, "Influence of KNO3 Bath Composition on Ion Exchange Process of Commercial Soda Lime Silicate Float Glass" INTECH, Chapter12.
Rehouma, F., Aiadi, K. E., "Glasses for Ion-exchange Technology", International Journal of Communications, Issue 4, vol. 1, 2006.
Ramaswamy, R.V. Planar, Buried, Ion-Exchanged Glass Waveguides: Diffusion Characteristics, IEEE Journal of Quantum Electronics, vol. QE, No. 6, Jun. 1986.
Danchevskaya, M.N., Torbin S. N., Martynova, L. F., Ivakin, Y. D., Muravieva, G. P., "Synthesis of Various Crystalline Modifications of Silicon Dioxide in Supercritical Water Fluid", Chemistry Department, Moscow State University, Leninskie Gory, 1/3, Moscow 119992, Russia.
Mehrer, H., "The Effect of Pressure on Diffusion", Defect and Diffusion Forum vols. 129-130 (1996) pp. 57-76.
Hiraiwa et al. "The solubility of silver nitrate in glycerine, ethylene glycol and 1,3-propanediol at 25oC". Analytical Letters, vol. 21, Issue 1, 1988.
Karlsson et al. "The technology of chemical glass strengthening—a review." Eur. J. Glass Sci. Technol. A, (2010) 52(2) p. 41-54.
Maggie Y. M. Lee, "Glass Part 3: New Generation of Specialty Glass for LCDs and AMOLEDs".

* cited by examiner

ANTIMICROBIAL AND STRENGTHENED-GLASS ARTICLES THROUGH PRESSURIZED ION EXCHANGE

This application claims the benefit of priority under 35 U.S.C. § 119 of U.S. Provisional Application Ser. No. 61/977,692 filed on Apr. 10, 2014 the content of which is relied upon and incorporated herein by reference in its entirety.

TECHNICAL FIELD

The present invention generally relates to antimicrobial and strengthened glass articles and methods for making them for various applications including but not limited to touch screens for various electronic devices, e.g., mobile phones, laptop computers, book readers, hand-held video gaming systems, and automated teller machines.

BACKGROUND

Ion-exchange processes are employed to vary and control the concentration of metal ions in various glass, glass-ceramic and ceramic substrates through localized compositional modifications. These compositional modifications in the substrates can be used to modify certain substrate properties. For example, alkali metal ions (e.g., Na and K ions) may be imparted into surface regions of substrates as a strengthening mechanism. As another example, various heavy metal ions (e.g., Ag, Cu and Zn ions) can be imparted into surface regions of substrates to provide the substrate with anti-microbial properties.

These ion-exchange processes often involve the immersion of substrates in a molten salt bath at elevated temperatures. The molten salt bath includes metal ions intended to be introduced into the substrates. Ions in the substrates are exchanged with the metal ions in the bath during the ion-exchange processes. Various ions are desirable for use in ion-exchange processes; however, many commercially available salts have high melting points far above ambient temperatures. The high melting points of these salts often exceed the stress point of the intended glass, ceramic, or glass-ceramic and cannot be used. In addition, molten salts often have high viscosities, an issue which can negatively influence the kinetics of ion-exchange processes using molten salts.

Accordingly, there is a need to develop systems and methods suitable for manufacturing operations that can be used to produce strengthened and antimicrobial glass, glass-ceramic, and ceramic articles.

SUMMARY

According to one embodiment, a method of treating a substrate in a pressure vessel is provided. The method includes: preparing a bath with a bath composition that comprises a polar solvent and a plurality of cations in a vessel; submersing a substrate in the bath; and pressurizing the bath in the vessel to a predetermined pressure (e.g., in the range from about 1.6 MPa to 22.6 MPa) that is substantially above ambient pressure. The method may include optionally heating the bath in the vessel to a predetermined temperature, which may be in the range from about 100° C. to 374° C. The method also includes treating the substrate for a predetermined duration in the bath. In some embodiments, the method includes exchanging or infusing a portion of the plurality of cations from the bath composition into an outer region of the substrate for a predetermined duration at the predetermined pressure, wherein the outer region extends from a first surface to a first selected depth in the substrate. The first selected depth may be in the range from 50 nm to 250 nm. In some embodiments, the method includes controlling the temperature and the pressure of the bath in the vessel such that a portion of the plurality of cations is exchanged or infused into the substrate. Controlling the pressure may include increasing the pressure of the bath substantially above ambient pressure. In some embodiments, controlling the pressure and temperature of the bath defines the outer region of the substrate, which extends from a plurality of substantially opposing surfaces of the substrate to the first selected depth. In some embodiments, the cations comprise $Ag^+$ ions, and the concentration of such cations at the plurality of substantially opposing surfaces is 6 atomic percent or greater.

In some embodiments, the substrate comprises a plurality of exchangeable cations that are exchanged with the portion of the plurality of cations in the bath composition. In one or more embodiments, the substrate may include a glass substrate or a glass-ceramic substrate. In some embodiments, the substrate includes a ceramic substrate and the portion of the plurality of cations from the bath composition is infused into the substrate. In some embodiments, the substrate includes a compressive stress layer extending from the first surface to a compressive stress layer. In such embodiments, the substrate may include an alkali glass composition.

The bath of one or more embodiments may include $H_2O$ and $AgNO_3$, and the plurality of cations comprises $Ag^+$ ions. In some embodiments, the polar solvent comprises a protic polar solvent or a aprotic polar solvent. Examples of suitable protic polar solvents include water, methanol, ethanol, isopropanol, 1,3-propanediol, nitromethane, formic acid, acetic acid, ethylene glycol and glycerol, and wherein the aprotic polar solvent is selected from the group consisting of acetone, ethyl acetate, acetonitrile, dimethyl sulfoxide, tetrahydrofurane and dimethylformamide. In one or more embodiments, the plurality of cations in the bath is derived from a salt or an acid. The acid may include silver nitrate, potassium sulfate, potassium hydroxide, potassium thiosulfate, potassium thioacetate, potassium monobasic phosphate, potassium dibasic phosphate, potassium tribasic phosphate, lithium nitrate, lithium sulfate, lithium chloride, cesium nitrate, cesium sulfate, rubidium nitrate, rubidium chloride, rubidium sulfate, erbium nitrate, erbium sulfate, hydrogen chloride, hydrogen sulfate, hydrogen carbonate, hydrogen phosphate, oxalic acid, hydrogen phosphate or combinations thereof. In some embodiments, the plurality of cations is derived from a salt with a melting point at or above 400° C.

According to a further embodiment, an article including a glass, glass-ceramic or a ceramic substrate having a reticulated configuration and an outer region extending from a surfaces to a first selected depth in the article is provided. In some embodiments, the outer region includes a plurality of substantially opposing surfaces that are separated by about 50 microns or less, a compressive stress layer extending from the plurality of substantially opposing surfaces to a compressive layer depth, which extends to or beyond the first selected depth, and a plurality of $Ag^+$ ions extending from the plurality of substantially opposing surfaces to an antimicrobial region depth, which extends to or beyond the first selected depth, wherein the antimicrobial region depth is greater than 50 nm and up to approximately 250 nm, the concentration of the $Ag^+$ ions at the plurality of substantially opposing surfaces is 6 atom percent or greater.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

Reference will now be made in detail to the present preferred embodiments, examples of which are illustrated in the accompanying drawings. Whenever possible, the same reference numerals will be used throughout the drawings to refer to the same or like parts.

Discussed herein are new methods for making antimicrobial and strengthened glass, glass-ceramic, and ceramic articles and substrates. The methods generally involve the use of an exchange process, infusion process or a combination thereof within a pressure vessel. The process is designed to strengthen and/or impart antimicrobial properties to the substrate via exposure of the substrate to alkali metal salts dissolved in a protic or aprotic polar solvent under super atmospheric pressures and elevated temperatures. Other embodiments of the process can incorporate acids and transition metals. In yet other embodiments the methods can be carried out on glass, glass-ceramic and ceramic articles and substrates. In yet more embodiments, the process can include additional steps including washing steps or additional baths designed to impart additional properties to the substrate.

Figure 1A:
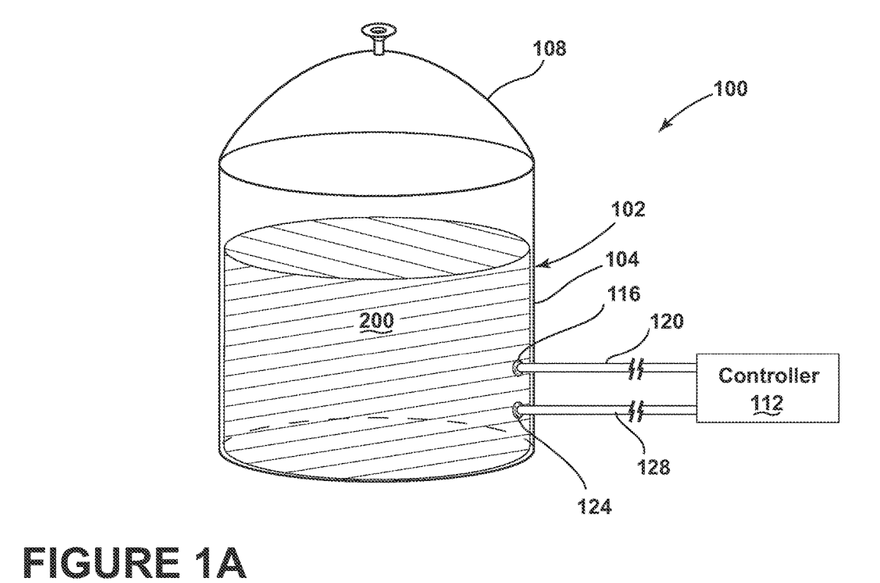
FIG. 1A is a schematic of a bath and pressure vessel employed in a system for producing the glass, ceramic, or glass-ceramic articles described herein, according to one embodiment.

Referring to FIG. 1A, a system 100 for producing the substrates and articles described herein is provided. The system 100 comprises a pressure vessel 102 having both a pressure vessel body 104 and a pressure vessel lid 108. The vessel 102 contains a bath 200. The bath 200 comprises a solvent and a plurality of ions or, specifically, cations, the ions being dissolved within the solvent. In one embodiment, the pressure vessel 102 can include a pressure sensor 116 and a temperature sensor 124. Both sensors can be connected to a controller 112 though a pressure coupling 120 and a temperature coupling 128, respectively. The controller 112 is capable of independently varying the temperature and the pressure within the pressure vessel 102 and the bath 200.

The solvent of bath 200 can comprise various solvent compositions. The solvent is preferably a polar liquid while at ambient temperature and pressure. The choice of polar solvent is not limited to particular compositions. For example, the solvent can be a protic polar solvent such as water, methanol, ethanol, isopropanol, nitromethane, formic acid, acetic acid, ethylene glycol, 1,3-propanediol, glycerol, or any other protic polar solvent or combination of protic polar solvents. Similarly, the polar solvent can also be an aprotic polar solvent such as acetone, ethyl acetate, acetonitrile, dimethyl sulfoxide, tetrahydrofuran, dimethylformamide, or any other aprotic polar solvent or combination of aprotic polar solvents. Further, the solvent may be a combination of protic and aprotic solvents in variable proportions.

The ions of the bath 200 employed in system 100 can comprise a variety of ions from a variety of sources. The ions may be introduced to the bath 200 from dissolution of salts, acids, and other known methods of introducing ions to a liquid. One family of salts that can be dissolved in the bath 200 includes metal salts. These metal salts can include transition metal ions including, but not limited to, copper, silver, chromium, nickel, cobalt, erbium, and iron. Exemplary salts can include silver nitrate, silver fluoride, silver perchlorate, copper (I) chloride, copper (I) acetate, copper (II) chloride, copper (II) nitrate, copper (II) sulfate, and erbium nitrate. Another exemplary sub-family of metal salts includes salts which comprise group 1A alkali metal ions. Such group 1A metal ions can include lithium, sodium, potassium, rubidium, and cesium. Exemplary salts containing these ions can include potassium sulfate, potassium hydroxide, potassium thiosulfate, potassium thioacetate, potassium monobasic phosphate, potassium dibasic phosphate, potassium tribasic phosphate, lithium nitrate, lithium sulfate, lithium chloride, cesium nitrate, cesium sulfate, rubidium nitrate, rubidium chloride, and rubidium sulfate. Yet another illustrative sub-family of metal salts that may be used is group 2A metal salts. Such group 2A metal ions include beryllium, magnesium, calcium, strontium, and barium. Metal salts of the group 2A variety can be dissolved in the polar solvent of the bath 200 in a similar manner as the other metal salts.

Acids may also serve as an ion source for bath 200 of system 100. Acids typically donate positively charged hydrogen ions and a variety of negatively charged ions. Exemplary acids include hydrogen sulfate, hydrogen chloride, hydrogen nitrate, hydrogen phosphate, hydrogen carbonate, oxalic acid. In the case of water, the free hydrogen ion reacts with the water to form a hydronium, or $H_3O^+$ ion, which can be used in an process employed in system 100.

Again referring to FIG. 1A, the controller 112 employed in the system 100 is capable of sensing the temperature and the pressure of the pressure vessel 102 and the bath 200. Controller 112 is also capable of coordinating the pressure within the pressure vessel 102 independently of the vessel temperature. Controller 112 can also perform a variety of other functions including controlling the duration at which the pressure vessel 102 and the bath 200 are kept at specific temperatures and pressures.

Figure 1B:
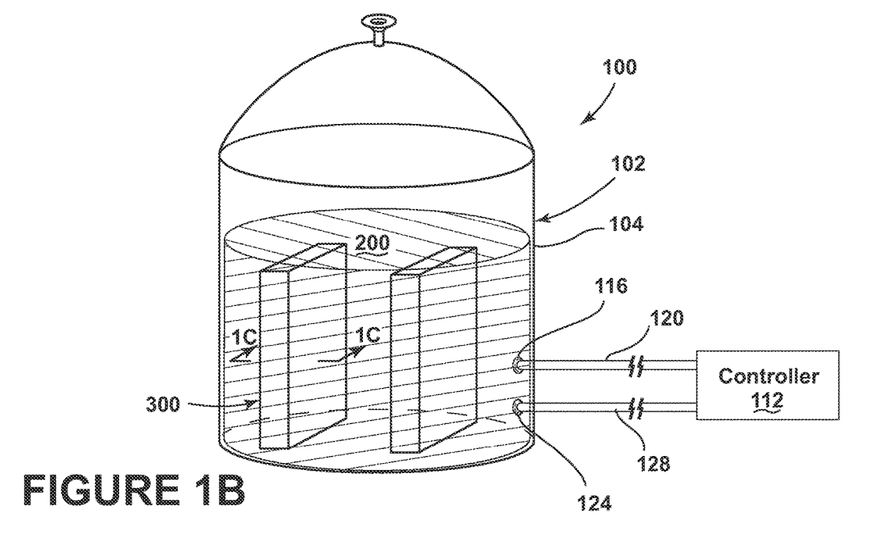
FIG. 1B is a schematic of the system depicted in FIG. 1A with substrates immersed in the bath and vessel according to another embodiment.

Referring to FIG. 1B, the substrates 300 are placed within the pressure vessel body 104 of the pressure vessel 102 employed in system 100 such that the substrates 300 are submerged in the bath 200. In one embodiment, the pressure vessel 102 of the system 100 is capable of heating the bath 200 to temperatures between 50° C. and 1000° C., and more preferably to temperatures between 80° C. and 500° C. Pressure vessel 102 of the system 100 can be capable of attaining and sustaining pressures between about 0.1 MPa and about 100 MPa. In some embodiments, vessel 102 can attain and sustain pressures between about 1.6 MPa and about 70 MPa. The pressure vessel 102 is capable of accepting substrates 300 of varying size and physical attributes. In one exemplary embodiment, the pressure vessel 102 is capable of accepting glass panels approximately 3.4 ft×4 ft. In another exemplary embodiment, the pressure vessel 102 is designed to accept glass panels approximately 6 ft×7 ft. In yet another embodiment, the pressure vessel 102 is capable of receiving multiple substrates 300 of different sizes and configurations. The design of the pressure vessel 102 is scalable in size and shape. Therefore, the pressure vessel 102 can be configured to fit various sizes and configurations of substrate 300 without appreciable loss of pressure or temperature in the bath 200 employed by system 100.

In one embodiment, the bath 200 employed in system 100 is prepared within the pressure vessel 102 prior to its use. In another embodiment, the bath 200 is prepared remotely from the pressure vessel 102 and is pumped or similarly conveyed into the vessel 102 at an appropriate time. In yet other embodiments, the bath 200 can be reused in the same vessel 102 or can be transferred to a different pressure vessel to carry out a similar process on a different substrate 300 or group of substrates 300.

Referring to FIG. 1B again, the substrate 300 can comprise or consist essentially of a glass, glass-ceramic, or ceramic substrate composition. The choice of glass used for the substrate 300 is not limited to a particular composition, as the properties described herein can be obtained using a variety of glass compositions. For example, the composition chosen can be any of a wide range of silicate, borosilicate, aluminosilicate, boroaluminosilicate, or soda lime glass compositions, which optionally can comprise one or more alkali and/or alkaline earth modifiers.

By way of illustration, one family of compositions that may be employed in the glass, ceramic, or glass-ceramic substrate 300 includes those having at least one of aluminum oxide or boron oxide and at least one of an alkali metal oxide or an alkali earth metal oxide, wherein $-15$ mol $\% \le (R_2O+R'O-Al_2O_3-ZrO_2)-B_2O_3 \le 4$ mol %, where R can be Li, Na, K, Rb, and/or Cs, and R' can be Mg, Ca, Sr, and/or Ba. One subset of this family of compositions includes from about 62 mol % to about 70 mol % $SiO_2$; from 0 mol % to about 18 mol % $Al_2O_3$; from 0 mol % to about 10 mol % $B_2O_3$; from 0 mol % to about 15 mol % $Li_2O$; from 0 mol % to about 20 mol % $Na_2O$; from 0 mol % to about 18 mol % $K_2O$; from 0 mol % to about 17 mol % MgO; from 0 mol % to about 18 mol % CaO; and from 0 mol % to about 5 mol % $ZrO_2$. Such glasses are described more fully in U.S. patent application Ser. No. 12/277,573, hereby incorporated by reference in its entirety as if fully set forth below.

Another illustrative family of compositions that may be employed in glass, ceramic, or glass-ceramic substrate 300 includes those having at least 50 mol % $SiO_2$ and at least one modifier selected from the group consisting of alkali metal oxides and alkaline earth metal oxides, wherein $[(Al_2O_3$ (mol %)$+B_2O_3$ (mol %))$/(\Sigma$ alkali metal modifiers (mol %))]>1. One subset of this family includes from 50 mol % to about 72 mol % $SiO_2$; from about 9 mol % to about 17 mol % $Al_2O_3$; from about 2 mol % to about 12 mol % $B_2O_3$; from about 8 mol % to about 16 mol % $Na_2O$; and from 0 mol % to about 4 mol % $K_2O$. Such glasses are described in more fully in U.S. patent application Ser. No. 12/858,490, hereby incorporated by reference in its entirety as if fully set forth below.

Yet another illustrative family of compositions that may be employed in glass, ceramic, or glass-ceramic substrate 300 includes those having $SiO_2$, $Al_2O_3$, $P_2O_5$, and at least one alkali metal oxide ($R_2O$), wherein $0.75 \le [(P_2O_5$ (mol %)$+R_2O$ (mol %))$/M_2O_3$ (mol %)]$\le 1.2$, where $M_2O_3=Al_2O_3+B_2O_3$. One subset of this family of compositions includes from about 40 mol % to about 70 mol % $SiO_2$; from 0 mol % to about 28 mol % $B_2O_3$; from 0 mol % to about 28 mol % $Al_2O_3$; from about 1 mol % to about 14 mol % $P_2O_5$; and from about 12 mol % to about 16 mol % $R_2O$. Another subset of this family of compositions includes from about 40 mol % to about 64 mol % $SiO_2$; from 0 mol % to about 8 mol % $B_2O_3$; from about 16 mol % to about 28 mol % $Al_2O_3$; from about 2 mol % to about 12 mol % $P_2O_5$; and from about 12 mol % to about 16 mol % $R_2O$. Such glasses are described more fully in U.S. patent application Ser. No. 13/305,271, hereby incorporated by reference in its entirety as if fully set forth below.

Yet another illustrative family of compositions that can be employed in glass, ceramic, or glass-ceramic substrate 300 includes those having at least about 4 mol % $P_2O_5$, wherein $(M_2O_3$ (mol %)$/R_xO$ (mol %))$<1$, wherein $M_2O_3=Al_2O_3+B_2O_3$, and wherein $R_xO$ is the sum of monovalent and divalent cation oxides present in the glass. The monovalent and divalent cation oxides can be selected from the group consisting of $Li_2O$, $Na_2O$, $K_2O$, $Rb_2O$, $Cs_2O$, MgO, CaO, SrO, BaO, and ZnO. One subset of this family of compositions includes glasses having 0 mol % $B_2O_3$. Such glasses are more fully described in U.S. Provisional Patent Application No. 61/560,434, the content of which is hereby incorporated by reference in its entirety as if fully set forth below.

Still another illustrative family of compositions that can be employed in a glass, ceramic, or glass-ceramic substrate 300 includes those having $Al_2O_3$, $B_2O_3$, alkali metal oxides, and contains boron cations having three-fold coordination. When strengthened (e.g., by ion exchange process), these glasses can have a Vickers crack initiation threshold of at least about 30 kilograms force (kgf). One subset of this family of compositions includes at least about 50 mol % $SiO_2$; at least about 10 mol % $R_2O$, wherein $R_2O$ comprises $Na_2O$; $Al_2O_3$, wherein $-0.5$ mol %$\le Al_2O_3$ (mol %)$-R_2O$ (mol %)$\le 2$ mol %; and $B_2O_3$, and wherein $B_2O_3$ (mol %)$-(R_2O$ (mol %)$-Al_2O_3$ (mol %))$\ge 4.5$ mol %. Another subset of this family of compositions includes at least about 50 mol % $SiO_2$, from about 9 mol % to about 22 mol % $Al_2O_3$; from about 4.5 mol % to about 10 mol % $B_2O_3$; from about 10 mol % to about 20 mol % $Na_2O$; from 0 mol % to about 5 mol % $K_2O$; at least about 0.1 mol % MgO and/or ZnO, wherein $0 \le MgO+ZnO \le 6$ mol %; and, optionally, at least one of CaO, BaO, and SrO, wherein 0 mol %$\le CaO+SrO+BaO \le 2$ mol %. Such glasses are more fully described in U.S. Provisional Patent Application No. 61/653,485, the content of which is incorporated herein by reference in its entirety as if fully set forth below.

As used herein, a liquid above its boiling temperature at ambient pressure is said to be "superheated." Polar solvents, such as water, employed in an exemplary embodiment of the system 100, can experience a change in the intermolecular forces which induces changes in the properties of the liquid. For example, a polar liquid can exhibit properties closer to that of an organic solvent. In another example, the superheated liquid has a viscosity that approaches zero as it approaches the critical temperature. By conducting the process within the pressure vessel 102 of system 100, these relationships can be exploited to obtain both manufacturing and product advantages.

Still referring to FIG. 1B, an exemplary treatment method includes steps of preparing a bath (e.g., bath 200) with a bath composition that comprises a polar solvent and a plurality of ions or cations in a vessel (e.g., vessel 102); and submersing a substrate (e.g., substrate 300) in the bath. In some embodiments, the substrate may include an outer region containing a plurality of ions that exchange with at least a portion of the plurality of the cations from the bath. The method then includes steps of pressurizing the bath in the vessel to a predetermined pressure substantially above ambient pressure; and optionally heating the bath in the vessel to a predetermined temperature and treating the substrate for a predetermined duration at the predetermined pressure and temperature such that a portion of the plurality of ions from the bath is exchanged or infused into the substrate. In some instances, a portion of the plurality of ions from the bath is exchanged with the plurality of ions in the substrate. In some embodiments, a portion of the plurality of ions from the bath is infused into the substrate. As used herein, the term "exchange" refers to the introduction of cations from a bath into the substrate (or a surface portion of the substrate) and replacement of other cations from the substrate having the same valence/charge/oxidation state as the cations from the bath. The term "exchange" may also include the replacement of other cations in the substrate having a different valence/charge/oxidation state as the cations from the bath. In one or more embodiments, the cations that are replaced (or exchanged) out of the substrate include alkali components. In one or more embodiments, the other cations that are replaced out of the substrate are non-alkali components of the substrate. As used herein, the term "infused" refers to the introduction of cations into the substrate (and specifically surface portions of the substrate) by a physical process in which the cations are introduced into interstitial space(s) in the substrate. The cations that are infused into the substrate are released from the substrate in specific environments. The predetermined duration, temperature and pressure can each be selected based at least in part on the substrate composition and the bath composition.

According to some embodiments, the method employing system 100 can be conducted for a predetermined time based on the composition of the bath 200, temperature of the bath 200, composition of the substrate 300, the pressure in the vessel 102 and/or the concentration of the exchangeable ions in the substrate 300. In yet other embodiments, the duration, bath temperature, and the pressure can be predetermined to define a region within the substrate 300. The region 324 is defined as the region between the substrate first surface 308 and the substrate first selected depth 312. The substrate first selected depth 312 can be at or above the depth limit of the substrate outer region 304. The substrate outer region 304 is the area within which ions from the bath 200 are exchanged or infused into the substrate 300 during the method employing the system 100.

Figure 1C:
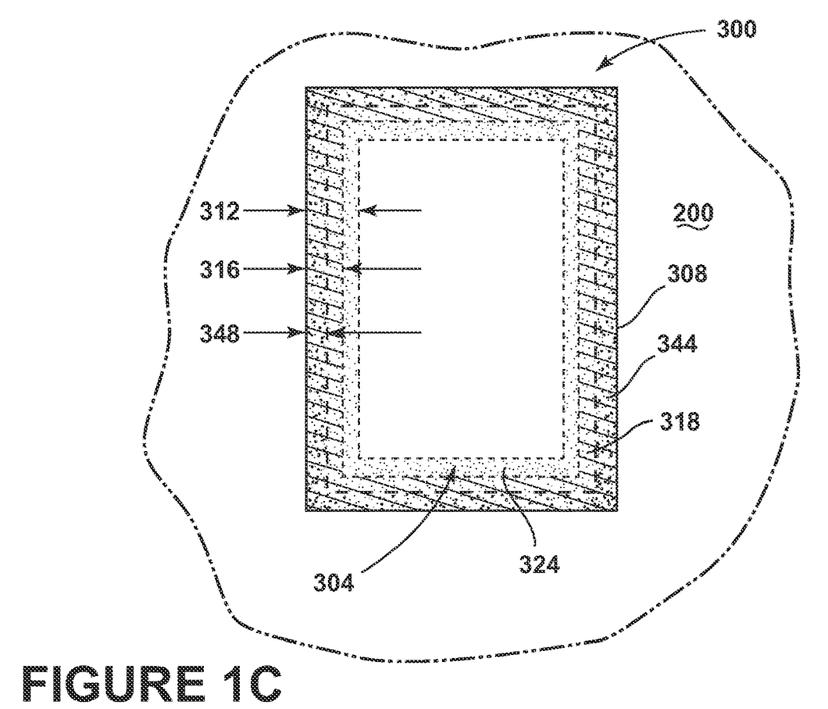
FIG. 1C is a cross-section of one of the substrates after completion of the process depicted in FIG. 1B according to a further embodiment.

Referring to FIGS. 1B and 1C, in an exemplary embodiment, substrate 300 can comprise a silicate glass composition having ion-exchangeable metal ions. The metal ions are exchangeable in the sense that exposure of the substrate 300 and substrate first surface 308 to the bath 200 containing ions can result in the exchange of some of the exchangeable metal ions in the substrate 300 with the ions from the bath 200. During the exchange, a plurality of exchangeable metal ions from the substrate 300 exchange through the substrate first surface 308 with a plurality of ions in the bath 200. The ions exchanged from the bath 200 into the substrate 300 to a first selected depth 312 thereby forming a region 324 within the substrate outer region 304. In some embodiments, the process employed in the 100 can comprise multiple exchange (and/or infusion) steps performed on substrate 300. During additional exchange and/or infusion processes (e.g., with a second bath 200 at a different pressure, time and duration), the ions of the bath 200 may exchange or infuse into the substrate 300 deeper than, or shallower than, previous processes. In such embodiments, the first selected depth 312 is the inner bound for the deepest exchanging or infusing process.

The infusion or exchange depth of the ions (e.g., to the first selected depth 312) is often referred to as the depth of layer ("DOL"). The DOL of substrates 300 may be about 15 nm or greater. In some instances, the DOL may be in the range from about 15 nm to about 50 nm, from about 20 nm to about 45 nm, or from about 30 nm to about 40 nm. In some embodiments, the DOL of substrate 300 can be dependent on the composition of the substrate 300 and/or the bath 200. In other embodiments, the DOL may also be dependent on the process conditions, such as temperature and pressure, within the pressure vessel 102 employed in the system 100.

In one or more embodiments, compressive stress levels are developed in the region 324 depicted in FIG. 1C. Compressive stresses are developed during the process in which a plurality of ions in substrate 300, and specifically ions contained between the substrate first selected depth 312 and the substrate first surface 308, is exchanged with a plurality of ions from the bath 200 having an ionic radius larger than the plurality of the ions from the substrate. In some embodiments the ions in the bath and the ions in the substrate are metal ions. As a result, a region 324 of the substrate 300 exhibits measurable compressive stress levels. The e metal ions in the substrate to be exchanged with the ions in the bath may be alkali metal ions such as lithium, sodium, potassium, and rubidium. The metal ions in the bath may be alkali metal ions such as sodium, potassium, rubidium, and cesium, with the proviso that the metal ions in the bath have an ionic radius greater than the ionic radius of the metal ions in the substrate.

As some of the ions from the bath 200 are distributed and otherwise incorporated into the substrate 300 at the expense of some of the ions originally in the substrate 300, a compressive stress layer 318 develops in the substrate 300 within the region 324. The compressive stress layer 318 extends from the substrate first surface 308 to a substrate compressive layer depth 316. In some embodiments, the compressive stress layer 318 can have a depth 316 above the substrate first selected depth 312, yet in other embodiments the depth 316 can be at the first selected depth 312.

In general, an appreciable concentration of the ions from the strengthening bath 200 (e.g., $K^+$ ions) exists in the compressive stress layer 318 of the substrate 300 after its submersion in the strengthening bath 200. These ions from the bath (e.g., $K^+$ ions) are generally larger than the ions in the substrate (e.g., $Na^+$ ions), thereby increasing the compressive stress level in the region 324 within the substrate 300. In addition, the amount of compressive stress associated with the compressive stress layer 318 and the depth of the substrate compressive layer depth 316 can each be varied (by virtue of the exchange process conditions employed in system 100, for example) based on the intended use of the substrate 300. In some embodiments, the compressive stress level in the compressive stress layer 318 is controlled such that tensile stresses generated within the substrate 300 as a result of the compressive stress layer 318 do not become excessive to the point of rendering the substrate 300 frangible. In some embodiments, the compressive stress level in the layer 318 may be about 200 MPa or greater. For example, the compressive stress level in the layer 318 may be up to about 700 MPa, about 800 MPa, about 900 MPa, or even about 1000 MPa.

Still referring to FIGS. 1B and 1C, in some embodiments the system 100 and in particular the pressure vessel 102, is capable of performing multiple step exchange and/or infusion processes on a single substrate 300 or a group of substrates 300. In some embodiments, the multi-step processes include additional strengthening treatments at different pressures and temperatures or treatments with different strengthening baths. In other embodiments, the additional exchanges and/or infusions employing system 100 can include the creation of new layers such as an antimicrobial region.

Referring now to FIG. 1C, in some embodiments, the bath 200 includes a plurality of silver ions that can provide an antimicrobial effect when incorporated into substrate 300. In some cases, the bath 200 may also include a plurality of metal ions consistent with those present in the substrate 300 and/or other ions. According to an exemplary embodiment, the bath 200 can possess a plurality of silver ions derived from dissolved $AgNO_3$, $AgF$, $AgClO_4$, or another silver salt with a concentration of about 5M. According to another exemplary embodiment, the bath 200 possesses a plurality of silver ions derived from $AgNO_3$ at a bath concentration of about 3M to 8M. In a further embodiment, the antimicrobial bath 200 comprises about 1M to 10M $AgNO_3$. It should also be understood that the plurality of silver ions from bath 200 can be incorporated into substrates strengthened from prior exchange steps or in non-strengthened substrates (e.g., non-strengthened soda lime glass substrates).

In an additional embodiment, the bath 200 possesses dissolved ions from $AgNO_3$, $KNO_3$ and $NaNO_3$ salts. In these embodiments, the presence of the $KNO_3$ and/or $NaNO_3$ constituents in the bath 200 helps prevent a significant quantity of strength-enhancing $K^+$ ions from being removed from the compressive stress layer 318 in the substrate 300 (e.g., for a method of using a system 100 in which a process is first used to strengthen the substrate 300 by the incorporation of $K^+$ ions).

According to some embodiments, the bath 200 containing antimicrobial ions can be employed at a temperature ranging from about 80° C. to about 500° C. and at a pressure between 0.16 MPa to 100 MPa. When antimicrobial bath 200 comprises dissolved $AgNO_3$ at a bath concentration of about 5M, bath 200 is preferably set at a temperature ranging from about 100° C. to about 374° C. and at a pressure from about 1.6 MPa to 70 MPa. In some embodiments, the pressure of the bath 200 may be between 1.6 MPa and 22.6 MPa. In certain embodiments, the bath 200 can be set in the range from about 80° C. to about 120° C.

In some embodiments, $Ag^+$ ions are imparted into the substrate region 324 of the substrate 300 using the system 100. The incorporation of the $Ag^+$ ions creates an antimicrobial region 344 between the substrate first surface 308 of the substrate 300 and the antimicrobial region depth 348. After an antimicrobial exchange and/or infusion process, the substrate first surface 308 can possess $Ag^+$ ions at an atomic concentration of about 5%, 10%, 15%, 20%, 25%, 30%, 35%, or 40%. In some embodiments, the duration of the exchange and/or infusion is controlled by system 100 based on the composition and temperature of bath 200, the pressure within the pressure vessel 102, and/or the composition of the substrate 300 to generate the desired antimicrobial properties associated with the substrate first surface 308. In some embodiments, the duration of the exchange and/or infusion process employed by system 100 to create antimicrobial region 344 is controlled from about 15 minutes (e.g., about 20 minutes or greater, about 25 minutes or greater, about 30 minutes or greater, or about 35 minutes or greater) to about 10 hours. In other embodiments, the duration of the exchange and/or infusion process to create layer 344 is from about 15 minutes to about 60 minutes. In some additional embodiments, the exchange and/or infusion process is controlled to a duration of about 25 minutes to about 35 minutes to create the layer 344. It should also be understood that, in some embodiments, $Ag^+$ ions can be incorporated into substrate 300 below the antimicrobial region depth 348 at concentrations that are not measurable with current analytical techniques and/or are not efficacious.

According to exemplary embodiments, the antimicrobial activity and efficacy obtained by employing the system 100 to produce the substrate 300 can be quite high. For example, it is expected that substrate 300 fabricated using system 100 described herein can exhibit at least a two log reduction (i.e., LR>~2 or kill rate of 99%) of at least *Staphylococcus aureus*, *Enterobacter aerogenes*, and *Pseudomonas aeruginosa* bacteria when tested according to the "dry" protocol described in U.S. Provisional Patent Application No. 61/908,401, which is hereby incorporated by reference in its entirety as if fully set forth below. This protocol is "dry" in the sense that the antimicrobial articles can be tested between about 23° C. and about 37° C. and at about 38% to 42% humidity. Preferably, the antimicrobial substrate 300 is tested at about 23° C. in about 42% humidity, and the substrate 300 is expected to demonstrate at least a two log reduction (i.e., LR>~2 or kill rate of 99%) of at least *Staphylococcus aureus*, *Enterobacter aerogenes*, and *Pseudomonas aeruginosa* bacteria when tested according to the "dry" protocol under these conditions. Further, a "dry" protocol for demonstrating the antimicrobial efficacy of substrate 300 fabricated with system 100 can include the steps: (a) inoculating nutrient agar with a portion of a stock having a plurality of bacterial organisms to form a culture; (b) incubating the culture to form a first incubated culture, incubating a portion of the first incubated culture with nutrient agar to form a second incubated culture, incubating a portion of the second incubated culture with nutrient agar to form a third incubated culture, and incubating the third incubated culture for approximately 48 hours to form an inoculated test plate with a plurality of bacterial colonies; (c) forming an inoculum by suspending a portion of the plurality of bacterial colonies in a buffered test solution, adjusting the test solution to a pH of approximately 7 to 8, and adding an organic soil serum at a concentration of approximately 10% to 30% by weight to the test solution; (d) inoculating the antimicrobial region of the antimicrobial article with a portion of the inoculum; (e) incubating the inoculated antimicrobial article for at least approximately two hours; and (f) washing the incubated and inoculated antimicrobial article in a neutralizing solution to form a residual test inoculum, counting the number of surviving bacterial colonies per volume in the residual test inoculum, and calculating the percent reduction in the number of surviving bacterial colonies in the residual test inoculum relative to a residual control inoculum.

The antimicrobial activity and efficacy of antimicrobial substrate 300, and such substrates fabricated with system 100 can also be demonstrated with an "ambient" protocol, based largely on Japanese Industrial Standard JIS Z 2801 (2000), entitled "Antimicrobial Products—Test for Antimicrobial Activity and Efficacy," the content of which is hereby incorporated by reference in its entirety as if fully set forth below. For example, the substrate 300 can be tested at about 23° C. and about 42% humidity for about 24 hours. Specifically, five (5) control samples and five (5) test samples can be used, wherein each sample has a specific inoculum composition and volume applied thereto, with a sterile coverslip applied to the inoculated samples to ensure uniform spreading on a known surface area. The covered samples can be incubated under the conditions described above, dried for about 6 to about 24 hours, rinsed with a buffer solution, and enumerated by culturing on an agar plate, the last two steps of which are similar to the procedure employed in the JIS Z 2801 (2000) test. Using this test, it is believed that the antimicrobial substrate 300 fabricated using system 100 described herein can exhibit at least a one log reduction (i.e., LR>~1 or a kill rate of 90%) of at least *Staphylococcus aureus* bacteria and at least a two log reduction (i.e., LR>~2 or a kill rate of 99.99%) of at least *Enterobacter aerogenes*, and *Pseudomonas aeruginosa* bacteria. In other implementations, it is believed that the antimicrobial substrate 300 described herein can exhibit at least a three log reduction (i.e., LR>~3 or a kill rate of 99.9%) of any bacteria to which they are exposed to under these testing conditions.

The antimicrobial activity and efficacy can also be measured in accordance with Japanese Industrial Standard JIS Z 2801 (2000), entitled "Antimicrobial Products Test for Antimicrobial Activity and Efficacy." Under the "wet" conditions of this test (i.e., about 37° C. and greater than 90% humidity for about 24 hours), it is believed that the antimicrobial substrate 300 fabricated using system 100 can exhibit at least a five log reduction (i.e., LR>~5 or a kill rate of 99.999%) of at least *Staphylococcus aureus, Enterobacter aerogenes*, and *Pseudomonas aeruginosa* bacteria. According to other embodiments, substrate 300 fabricated using system 100 can exhibit at least a two log reduction (i.e., LR>~2 or kill rate of 99%) of at least *Staphylococcus aureus, Enterobacter aerogenes*, and *Pseudomonas aeruginosa* bacteria when tested according to the protocol described in U.S. Provisional Patent Application No. 61/908,401.

More generally, substrates 300 fabricated according to the process described herein may have exceptional antimicrobial properties with enhanced strength levels consistent with or higher than that exhibited by Corning® Gorilla® glass. These substrates 300 also are produced at relatively low cost. This is due in part to the shallow, but still efficacious, levels of $Ag^+$ imparted in the substrate 300 (e.g., to the antimicrobial region depth 348) using system 100. The low cost is also due to the relatively low temperatures (and higher pressures) of the antimicrobial bath 200 employed in system 100, as compared to the temperature of the bath employed in conventional molten salt bath processes.

In order to initiate exchange and/or infusion using system 100, an activation energy barrier must be overcome to allow substrate ions and bath ions to migrate in and out of the bath 200 and the substrate 300 or to allow the bath ions to infuse out of the bath 200 and into the substrate 300. Both temperature and pressure can serve as an energy source to overcome the activation energy; however, some nominal increased temperature is typically required. According to some embodiments, a process employing system 100 can be carried out in the pressure vessel 102 below the atmospheric boiling point of the bath 200 at a super-atmospheric pressure. In other embodiments, the process can be carried out with the temperature of the bath 200 set below the stress point of the substrate 300 at a super-atmospheric pressure. In such embodiments, the pressure of the bath 200 can be between 0.16 MPa and 100 MPa, more particularly 1.6 MPa and 70 MPa, and even more particularly between 1.6 MPa and 22.6 MPa. In these exemplary embodiments both the temperature and the pressure of the bath 200 employed in system 100 may provide the activation energy to initiate exchange and/or infusion between the bath 200 and the substrate 300. One advantage of using the system 100 at a super-atmospheric pressure is that the temperature of the bath 200 can be minimized without appreciably increasing the process duration. In some embodiments, the reduction in the temperature of the bath 200 allows the substrate 300 to be configured with a functional or decorative layer that is sensitive to heat. Exemplary functional layers include, but are not limited to, touch screen patterning, scratch resistant coatings, and other protective features for use in consumer electronics. Another advantage that can be realized from these embodiments of system 100 is a decrease in production costs associated with the lower temperatures needed for the exchange and/or infusion.

In some embodiments, the ions of the bath 200 comprise ions from high melting temperature salts as determined relative to the stress point of the composition of the substrate 300. In further embodiments, the ions in the bath 200 come at least in part from salts having a melting temperature above 400° C. In other embodiments, the melting temperature of the salts is above the stress point of the substrate 300 (e.g., glass, glass-ceramic, or ceramic) being in system 100. One advantage derived from dissolving salts in polar solvents is that temperatures high enough to damage the substrate 300 are not required during the process employed in system 100. The dissolution of the salts in the solvent of the bath 200 allows free ions to make contact with the substrate outer region 304 at temperatures lower than the melting point of the salt. Therefore, the bath 200 can employ salts with melting temperatures higher than the stress point of the substrate 300 (e.g., glass, glass-ceramic, or ceramic) that is being exchange and/or infusion. Exemplary high temperature salt families that may be used in the ion-exchange process of system 100 include group 1A alkali metal sulfates, group 2A alkali metal salts and transition metal salts.

In other embodiments, the system 100 can employ a pressure vessel 102 that includes a bath 200 comprising a high critical point solvent and a substrate 300 with a glass composition having a high stress point. Arranged in this fashion, the system 100 can be used to employ pressure vessel 102 for conducting the ion exchange at a temperature above 400° C. and a pressure above 40 MPa. In such embodiments, the duration of the exchange and/or infusion can be shortened due to an increased exchange and/or infusion rate resulting from the high temperatures and pressures.

Another aspect in the initiation of the process in system 100 is the concentration of salts and/or acids in the bath 200 and the magnitude of the concentration gradient between the bath 200 and the substrate 300. In some embodiments, the concentration of salts or acids in the bath 200 can range from unsaturated to supersaturated at ambient temperature, and more particularly from saturated to supersaturated at ambient temperature. In other embodiments, the salt or acid concentration in the bath 200 can be supersaturated at ambient temperatures and pressures, but saturated at the predetermined processing temperatures and pressures. One advantage of the bath 200 reaching a superheated state is the increased capability of the bath 200 to carry dissolved ions. Another advantage of the superheated bath 200 is that a salt or acid having low solubility in the solvent at ambient temperatures may have high solubility in the superheated state. The increased ability to hold solute ions creates a greater concentration gradient between the bath 200 and the substrate 300. This increased concentration gradient can positively affect the exchange rate between the substrate 300 and the bath 200, thereby shortening the duration required to develop a predetermined or desired first depth 312 and region 324.

In one exemplary embodiment, the pressure vessel 102 employed in system 100 is capable of recycling the bath 200, including both the polar solvent and the precious metals of the salts. In one embodiment, superheated solvent (e.g., heated during an exchange and/or infusion step) can be recycled for use in a washing step as a washing liquid to wash excess and deposited salts from the surface of the substrate 300. In another embodiment, the superheated solvent can be screened or filtered prior to the washing step to increase the cleanliness of the substrate 300. In such embodiments, the filtered salts can be reintroduced in later exchanges and/or infusions to reduce material costs. Such a washing step saves processing time by eliminating the need to transfer the substrate 300 to a separate cleaning line. The washing step also minimizes energy and material use by eliminating the need to heat another solvent for use in the washing step. In another embodiment, the washing liquid can be recycled and used again as a bath 200 in system 100 until the percentage of desired exchange and/or infusion falls below a predetermined minimum value.

Another exemplary method of treating a substrate in a pressure vessel (e.g., pressure vessel 102) employing an process includes the steps of preparing a bath (e.g., bath 200) comprising a polar solvent and a plurality of ions in a vessel (e.g., vessel 102); and submersing a substrate (e.g., rolled substrate 328) in the ion-exchange bath. The substrate may include an outer region containing a plurality of ions. The outer region (e.g., outer region 330) can comprise a plurality of substantially opposing surfaces (e.g., opposing surfaces 330*a*, 330*b*) separated by 50 microns or less. The exemplary method also includes the step of controlling the temperature and the pressure of the bath in the vessel such that a portion of the plurality of ions from the bath is exchanged or infused into the substrate. The pressure of the bath can be raised substantially above ambient pressure during the controlling step. Further, the substrate can consist essentially of a glass, glass-ceramic or ceramic composition.

Figure 2A:
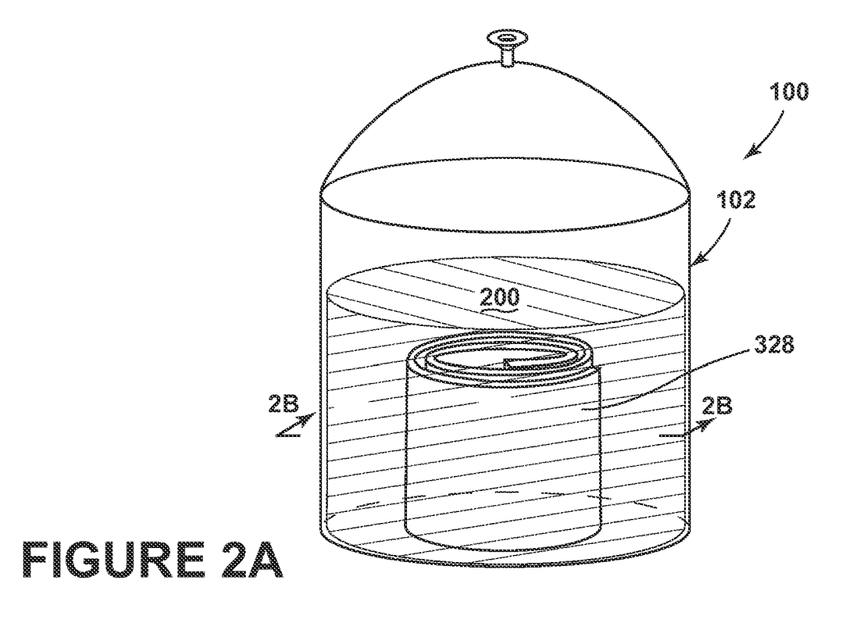
FIG. 2A is a schematic of a substrate immersed in a bath in a pressure vessel employed in a system according to an embodiment.
Figure 2B:
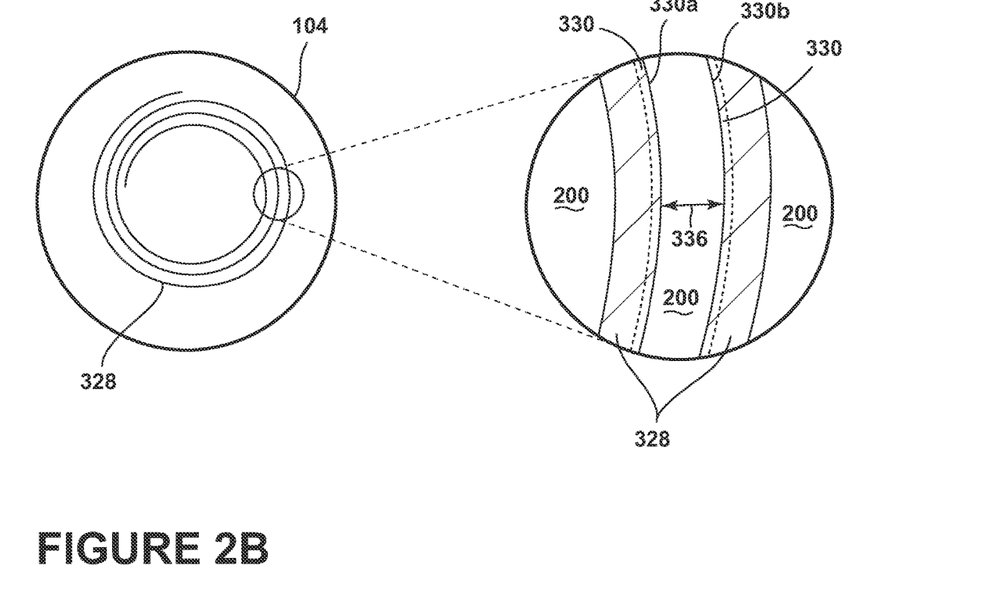
FIG. 2B is an enlarged cross-section of the substrate depicted in FIG. 2A after completion of the process.

Referring to FIGS. 2A and 2B, the system 100*a* is substantially similar to the system 100 outlined earlier in the disclosure. Like-numbered elements described in connection with system 100*a* and system 100 operate and/or are configured the same as one another. In some embodiments, a system 100*a* can be employed with an method to treat a substrate 328 having a plurality of substantially opposing surfaces 330*a* and 330*b*. In other embodiments, the substrate 328 can be configured in a rolled or substantially rolled configuration while being treated in the pressure vessel 102 using system 100*a*. Exemplary substrates 328 that may be treated using system 100*a* include Corning® Willow® glass and other flexible glasses. FIG. 2A illustrates a substantially rolled substrate 328 submerged in the bath 200. FIG. 2B shows a top down view of a cross section of the rolled substrate 328 and pressure vessel 102 depicted in FIG. 2A. As shown in FIG. 2B, a distance 336 is defined between substantially opposing surfaces 330*a* and 330*b* of the rolled substrate outer region 330 of the substrate 328. The bath 200 is capable of flowing between the substantially opposing surfaces 330*a* and 330*b*. In one embodiment, the distance 336 can be 50 nm or less. In other embodiments, the distance can be 25 µm or less, and more particularly 10 µm or less. In yet more embodiments, the distance 336 can be less than 500 nm.

As disclosed above, the superheating of the bath 200 in system 100 can decrease the viscosity of the bath 200. Bath 200 employed in system 100*a* can also be superheated in this fashion. The decrease in viscosity allows the bath 200 to flow between the substantially opposing surfaces 330*a* and 330*b* and facilitates exchange and/or infusion with substrate 328. Accordingly, the region 324, the compressive stress layer 318, and/or the antimicrobial region 344 can each extend from the substantially opposing surfaces 330*a* and 330*b* to selected depths within the substrate 328 (e.g., first selected depth 312 or compressive stress layer depth 316). As the viscosity of the bath 200 approaches 0, the theoretical limit for where the bath 200 may flow in and around substrate 328 approaches the actual size of the bath ions and solvent molecules. Thus, in some embodiments of system 100*a*, the distance 336 between substantially opposing surfaces 330*a* and 330*b* can be on the nanometer, picometer and/or atomic scale.

In some embodiments, the substrate substantially opposing surfaces 330*a* and 330*b* can be formed by a rolled or substantially rolled configuration as depicted in FIG. 2A and FIG. 2B. In other embodiments, the substrate 328 can be corrugated or contain fine ridges along its surface. In yet other configurations, the substrate 328 can be an object having protrusions spaced closely together or can contain internal voids with openings to the surface. In yet more embodiments, the substantially opposing surfaces 330*a* and 330*b* may not be contained on a single substrate, but may be opposing surfaces on different substrates. For example, multiple substrates may be loaded in the pressure vessel 102 employed in system 100 such that the distance 336 between substrate surfaces may define the substantially opposing surfaces 330*a* and 330*b*. The distances between substrates 328 in such embodiments can be 50 µm or less, 40 µm or less, 30 µm or less, 20 µm or less, and 10 µm or less. In some embodiments, this distance 336 can be less than 500 nm.

By employing some of the exemplary methods described above with systems 100 or 100*a*, an article (e.g., substrate 300, substrate 328) having a region (e.g., region 324) can be produced. Such an article can comprise: (a) a composition that consists essentially of a glass, glass-ceramic or a ceramic composition; and (b) an outer region (e.g., outer region 304) that comprises a plurality of substantially opposing surfaces separated by 50 microns or less. The outer region can comprise a region extending from the plurality of substantially opposing surfaces to a first selected depth in the article (e.g., from surfaces 330*a* and 330*b* to first selected depth 312).

Figure 3A:
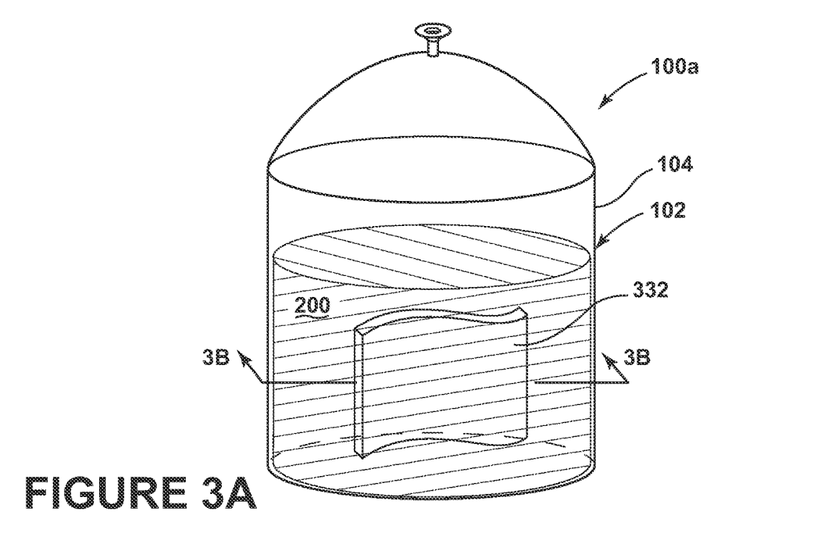
FIG. 3A is a schematic of a substrate immersed in a bath in a pressure vessel employed in a system according to an embodiment.
Figure 3B:
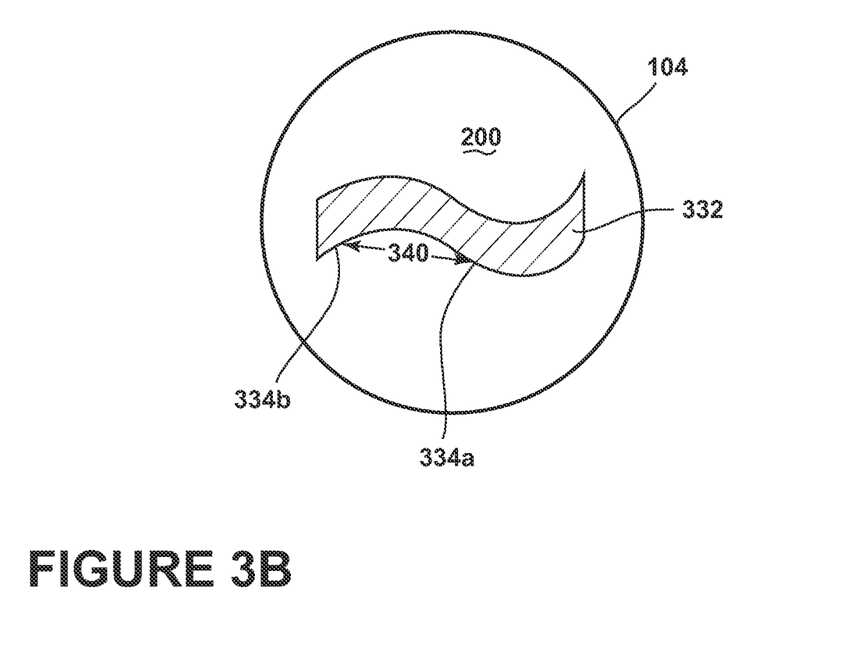
FIG. 3B is an enlarged cross-section of the substrate depicted in FIG. 3A after completion of the process.

Referring to FIGS. 3A and 3B, a substrate 332 can be placed in the pressure vessel 102 in a variety of configurations or have a variety of configurations when system 100*a* is employed to treat the substrate. In some embodiments, the substrate 332 is a flexible glass, glass-ceramic or ceramic which can be treated in an as-produced configuration within the pressure vessel 102.

In some embodiments, a substrate 332 with a substantially reticulated configuration may be submerged in the bath 200 using system 100a. FIG. 3A illustrates a substantially reticulated substrate 332 while it is submerged in the bath 200 in the pressure vessel 102 of system 100a. FIG. 3B shows a top down view of a cross-section of reticulated substrate 332 and pressure vessel 102. In some embodiments, the reticulated substrate 332 can have a plurality of substantially opposing substrate surfaces 334a, 334b. In some embodiments the distance 340 can be 50 μm or less, 40 μm or less, 30 μm or less, 20 μm or less, and 10 μm or less. In other embodiments, the distance 340 can be less than 500 nm. Similarly, the reticulated substrate 332 can include other features such as it being curved and/or sharply-bent. Similarly, the substrate 332 can be a single unitary object, a multi-layered structure, or a laminate.

While the embodiments disclosed herein have been set forth for the purpose of illustration, the foregoing description should not be deemed to be a limitation on the scope of the disclosure or the appended claims. It will be apparent to those skilled in the art that various modifications and variations can be made without departing from the spirit or scope of the claims.

What is claimed is:

1. A method of treating a substrate in a pressure vessel, comprising:
    preparing a bath with a bath composition that comprises a polar solvent and a plurality of cations comprising a plurality of $Ag^+$ ions and a plurality of $K^+$ ions in a vessel;
    submersing a substrate in the bath, wherein the substrate comprises a plurality of exchangeable cations;
    pressurizing the bath in the vessel to a predetermined pressure, wherein the predetermined pressure is substantially greater than ambient pressure; and
    exchanging or infusing a portion of the plurality of cations from the bath composition with a portion of the plurality of exchangeable cations in an outer region of the substrate for a predetermined duration at the predetermined pressure, wherein the outer region extends from a first surface to a first selected depth in the substrate, and further wherein the exchanging or infusing is conducted to form (a) a compressive stress layer having a portion of the plurality of $K^+$ ions that extends from a first surface of the substrate to a compressive layer depth and (b) an antimicrobial region having a portion of the plurality of $Ag^+$ ions that extends from the first surface to an antimicrobial region depth.

2. The method according to claim 1, wherein the substrate comprises a glass substrate or glass-ceramic substrate.

3. The method according to claim 1, wherein the substrate comprises a ceramic substrate and the portion of the plurality of cations from the bath composition is infused into the substrate.

4. The method according to claim 1, wherein the bath comprises $H_2O$ and $AgNO_3$.

5. The method according to claim 1, wherein the predetermined pressure is in the range from about 1.6 MPa to 22.6 MPa.

6. The method according to claim 1, further comprising heating the bath in the vessel to a predetermined temperature in the range from about 100° C. to 374° C.

7. The method according to claim 1, wherein the first selected depth is in the range from about 50 nm to about 250 nm.

8. The method according to claim 1, wherein the polar solvent is a protic polar solvent or a aprotic polar solvent, wherein the protic polar solvent is selected from the group consisting of water, methanol, ethanol, isopropanol, 1,3-propanediol, nitromethane, formic acid, acetic acid, ethylene glycol and glycerol, and wherein the aprotic polar solvent is selected from the group consisting of acetone, ethyl acetate, acetonitrile, dimethyl sulfoxide, tetrahydrofurane and dimethylformamide.

9. The method according to claim 1, wherein the plurality of cations is derived from a salt or an acid selected from the group consisting of silver nitrate, potassium sulfate, potassium hydroxide, potassium thiosulfate, potassium thioacetate, potassium monobasic phosphate, potassium dibasic phosphate, potassium tribasic phosphate, lithium nitrate, lithium sulfate, lithium chloride, cesium nitrate, cesium sulfate, rubidium nitrate, rubidium chloride, rubidium sulfate, erbium nitrate, erbium sulfate, hydrogen chloride, hydrogen sulfate, hydrogen carbonate, hydrogen phosphate, oxalic acid and hydrogen phosphate.

10. The method according to claim 8, wherein the plurality of cations is derived from a salt with a melting point at or above 400° C.

11. A method of treating a substrate in a pressure vessel, comprising the steps:
    providing a bath comprising a polar solvent and a plurality of cations comprising a plurality of $Ag^+$ ions and a plurality of $K^+$ ions in a vessel;
    submersing a substrate in the bath, wherein the substrate comprises a plurality of exchangeable cations; and
    controlling the temperature and the pressure of the bath in the vessel such that a portion of the plurality of cations is exchanged or infused into with a portion of the exchangeable cations in the substrate to form (a) a compressive stress layer having a portion of the plurality of $K^+$ ions that extends from a first surface of the substrate to a compressive layer depth and (b) an antimicrobial region having a portion of the plurality of $Ag^+$ ions that extends from the first surface to an antimicrobial region depth,
    wherein the pressure of the bath is increased substantially above ambient pressure during the controlling step, and further wherein the substrate comprises a glass, glass-ceramic or ceramic composition.

12. The method according to claim 11, wherein the step for controlling the temperature and the pressure of the bath defines an outer region into which the portion of the plurality of cations is exchanged or infused into the substrate, wherein the outer region extends from a plurality of substantially opposing surfaces of the substrate to a first selected depth in the substrate.

13. The method according to claim 12, wherein the substrate comprises an alkali glass composition, and the outer region further comprises the compressive stress layer extending from the plurality of substantially opposing surfaces to the compressive layer depth.

14. The method according to claim 11, wherein the bath comprises $H_2O$ and $AgNO_3$.

15. The method according to claim 11, wherein the step for controlling the temperature and the pressure of the bath comprises controlling the pressure to approximately 1.6 MPa to 22.6 MPa, and the temperature to approximately 100° C. to 374° C.

16. The method according to claim 12, wherein the first selected depth is greater than 50 nm and up to approximately 250 nm, and the concentration of the cations at the plurality of substantially opposing surfaces is 6 atom percent or greater.

17. The method according to claim 11, wherein the plurality of cations is derived from a salt or an acid selected from the group consisting of silver nitrate, potassium sulfate, potassium hydroxide, potassium thiosulfate, potassium thioacetate, potassium monobasic phosphate, potassium dibasic phosphate, potassium tribasic phosphate, lithium nitrate, lithium sulfate, lithium chloride, cesium nitrate, cesium sulfate, rubidium nitrate, rubidium chloride, rubidium sulfate, erbium nitrate, erbium sulfate, hydrogen chloride, hydrogen sulfate, hydrogen carbonate, hydrogen phosphate, oxalic acid and hydrogen phosphate.

* * * * *

UNITED STATES PATENT AND TRADEMARK OFFICE
CERTIFICATE OF CORRECTION

PATENT NO.       : 10,472,278 B2
APPLICATION NO.  : 15/303143
DATED            : November 12, 2019
INVENTOR(S)      : Arthur Winston Martin et al.

Page 1 of 1

It is certified that error appears in the above-identified patent and that said Letters Patent is hereby corrected as shown below:

In the Claims

In Column 16, Line 37, Claim 11, after "infused" delete "into".

Signed and Sealed this
Eleventh Day of February, 2020

Andrei Iancu
*Director of the United States Patent and Trademark Office*